US010844277B2

(12) United States Patent
Ndong et al.

(10) Patent No.: US 10,844,277 B2
(45) Date of Patent: Nov. 24, 2020

(54) SELF-DIVERTING ACIDIZING SYSTEM

(71) Applicant: RHODIA OPERATIONS, Paris (FR)

(72) Inventors: Rose Ndong, Plainsboro, NJ (US);
Juliette Triquet, Bois-Colombes (FR);
Genyao Lin, Pittsburgh, PA (US);
Subramanian Kesavan, East Windsor,
NJ (US); Louis Villafane, Pittsburgh,
PA (US); Jian Zhou, Langhorne, PA
(US); Ahmed Rabie, Willingboro, NJ
(US)

(73) Assignee: RHODIA OPERATIONS,
Aubervilliers (FR)

( * ) Notice: Subject to any disclaimer, the term of this
patent is extended or adjusted under 35
U.S.C. 154(b) by 0 days.

(21) Appl. No.: 15/604,839

(22) Filed: May 25, 2017

(65) Prior Publication Data
US 2017/0342314 A1 Nov. 30, 2017

Related U.S. Application Data

(60) Provisional application No. 62/341,254, filed on May 25, 2016.

(51) Int. Cl.
E21B 43/25 (2006.01)
C09K 8/74 (2006.01)
C07C 233/36 (2006.01)
C07C 309/14 (2006.01)
C09K 8/66 (2006.01)
C09K 8/72 (2006.01)
E21B 41/02 (2006.01)

(52) U.S. Cl.
CPC .............. C09K 8/74 (2013.01); C07C 233/36
(2013.01); C07C 309/14 (2013.01); C09K
8/665 (2013.01); C09K 8/725 (2013.01); E21B
41/02 (2013.01); E21B 43/25 (2013.01)

(58) Field of Classification Search
None
See application file for complete search history.

(56) References Cited

U.S. PATENT DOCUMENTS

| 5,789,349 | A * | 8/1998 | Patel ........................ C09K 8/24 507/118 |
| 5,916,967 | A | 6/1999 | Jones et al. |
| 7,279,446 | B2 | 10/2007 | Colaco et al. |
| 7,427,583 | B2 | 9/2008 | Couillet et al. |
| 7,759,292 | B2 | 7/2010 | Eoff et al. |
| 9,080,043 | B2 | 7/2015 | Yuan-Huffman et al. |
| 2004/0043905 | A1 * | 3/2004 | Miller ...................... C09K 8/32 507/100 |
| 2005/0107265 | A1 | 5/2005 | Sullivan et al. |

(Continued)

FOREIGN PATENT DOCUMENTS

EP 0875557 B1 12/2005
WO 2012080382 A1 6/2012
(Continued)

Primary Examiner — Andrew Sue-Ako

(57) ABSTRACT

A method of acidizing a formation penetrated by a wellbore that includes the steps of injecting into the wellbore at a pressure below formation fracturing pressure a treatment fluid that includes a gelling fluid including a gelling agent and a hydrophobically-modified associative polymer, and an aqueous acid; and allowing the treatment fluid to acidize the formation.

11 Claims, 4 Drawing Sheets

(56) References Cited

U.S. PATENT DOCUMENTS

| | | |
|---|---|---|
| 2005/0107503 A1 | 5/2005 | Couillet et al. |
| 2005/0194140 A1* | 9/2005 | Dalrymple ........... C09K 8/5083 166/279 |
| 2007/0032386 A1* | 2/2007 | Abad ................... C09K 8/5751 507/201 |
| 2007/0281869 A1 | 12/2007 | Drochon et al. |
| 2009/0111716 A1 | 4/2009 | Hough et al. |
| 2011/0048718 A1* | 3/2011 | Van Zanten ............. C09K 8/12 166/305.1 |
| 2011/0053812 A1* | 3/2011 | Ezell ...................... C09K 8/035 507/219 |
| 2011/0105369 A1 | 5/2011 | Reddy |
| 2011/0262293 A1 | 10/2011 | Heinzel et al. |
| 2014/0166291 A1 | 6/2014 | Friesen et al. |
| 2014/0262293 A1 | 9/2014 | Song et al. |
| 2017/0327733 A1 | 11/2017 | Li et al. |

FOREIGN PATENT DOCUMENTS

| | | |
|---|---|---|
| WO | 2014164078 | 10/2014 |
| WO | 2015171140 A1 | 11/2015 |

\* cited by examiner

SELF-DIVERTING ACIDIZING SYSTEM

CROSS-REFERENCE TO RELATED APPLICATION

The present application claims the benefit of priority under 35 U.S.C. § 119(e) of U.S. Provisional Application Ser. No. 62/341,254, filed on May 25, 2016, the entire disclosure of which is incorporated herein by reference.

BACKGROUND

There are several stimulation treatments for increasing oil production, such as hydraulic fracturing and acidizing. Hydraulic fracturing includes pumping specially-engineered fluids at high pressures into the formation in order to create fissures that are held open by the proppants present in the fluid once the treatment is completed.

In contrast, acidizing is used for low permeability formations. It includes injecting acid into the formation. The acid then reacts with soluble substances of the formation, creating pathways for oil conductivity.

SUMMARY

Figure 1:
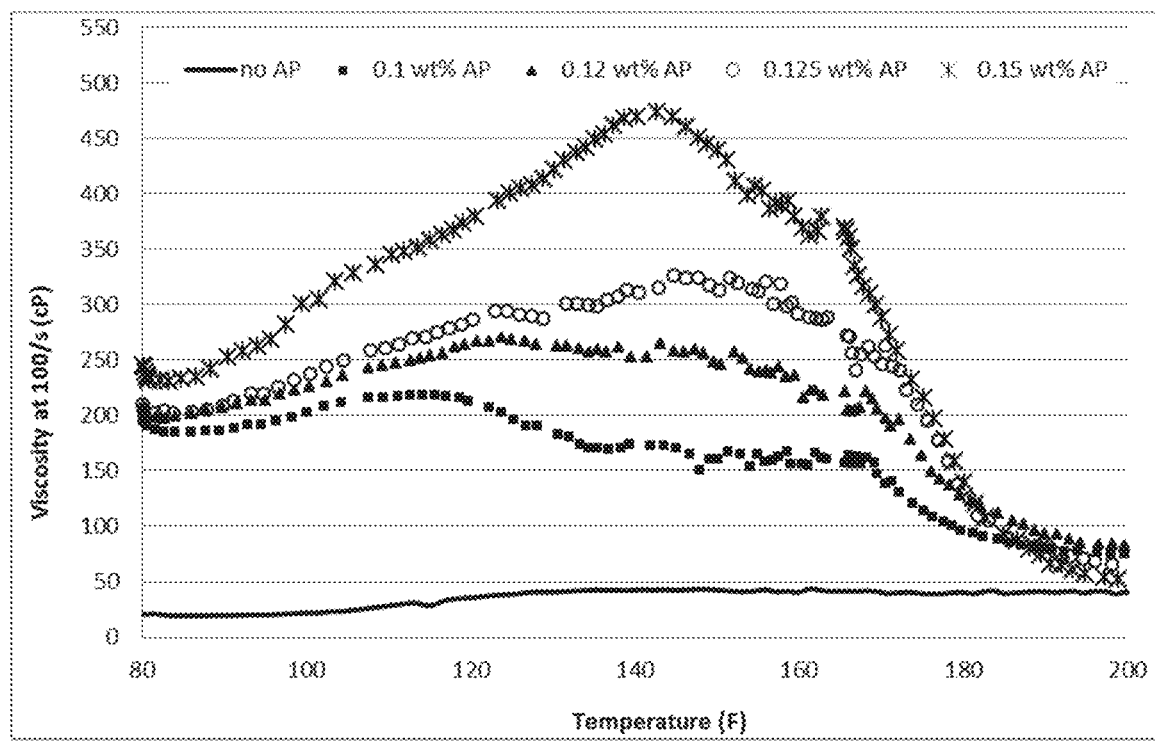
FIG. 1 is a plot depicting viscosity enhancement of the gelling agent surfactant upon addition of the hydrophobically-modified associative polymer (AP)

The present disclosure provides a method of acidizing a formation penetrated by a wellbore that includes the steps of injecting into the wellbore at a pressure below formation fracturing pressure a treatment fluid that includes a gelling fluid including a gelling agent and a hydrophobically-modified associative polymer, and an aqueous acid; and allowing the treatment fluid to acidize the formation. In an embodiment, the method further includes the step of allowing the treatment fluid to self-divert into the formation.

Also described is a method of treating an oilfield well that includes the step of injecting into the well a fluid that includes: (i) a gelling agent and (ii) a hydrophobically-modified associative polymer in an amount below its C* concentration.

In an embodiment, the gelling agent includes a surfactant selected from Formulas I, II, III, IV, and combinations thereof. In an embodiment, the hydrophobically-modified associative polymer (AP) includes at least one water-soluble part selected from acrylamide, methacrylamide, acrylic acid, methacrylic acid, 2-acrylamidomethylpropanesulfonic acid, N-vinyl pyrrolidone, N-vinyl formamide, and mixtures thereof. In another embodiment, the AP includes at least one water-insoluble part selected from the group consisting of straight or branched alkyl or alkylaryl alcohol esters of acrylic or methacrylic acid, straight or branched alkyl or alkylaryl amides of acrylamide or methacrylamide, styrene, butadiene, 1-vinylnaphthalene, and mixtures thereof.

DETAILED DESCRIPTION

The present disclosure relates to methods of using gelling fluids for acidizing a formation. In an embodiment, the gelling fluid includes a gelling agent and a hydrophobically-modified associative polymer (AP). As described herein, the gelling agent includes one or more surfactant-based molecules.

In an embodiment, the gelling fluid includes a gelling agent selected from Formulas I, II, III, IV, and combinations thereof:

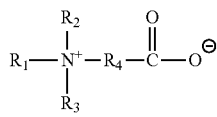

Formula I

In Formula I, $R_1$ is selected from alkyl, alkenyl, alkylarylalkylene, alkenylarylalkylene, alkylaminoalkylene, alkenylamino-alkylene, alkylamidoalkylene, or alkenylamidoalkylene, wherein each of said alkyl groups contain from about 14 to about 24 carbon atoms and may be branched or straight chained and saturated or unsaturated, and wherein said alkylene groups have from about 1 to about 6 carbon atoms. $R_2$, $R_3$ and $R_4$ are the same or different and are alkyl or hydroxyalkyl of from 1 to about 5 carbon atoms, or $R_3$ and $R_4$ or $R_2$ together with the nitrogen atom to which they are bonded form a heterocyclic ring of up to 6 members.

In an embodiment, the gelling agent of Formula I is selected from oleyl amidopropyldimethyl betaine:

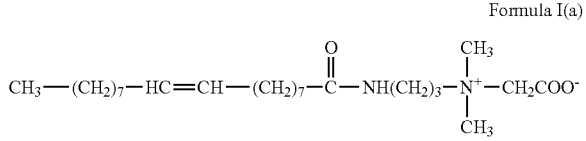

Formula I(a)

and tallow dihydroxyethyl glycinate:

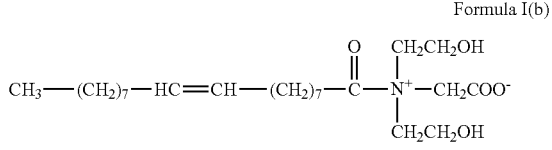

Formula I(b)

In Formula II, $R_1$ is a hydrocarbyl group that may be branched or straight-chain, aromatic, aliphatic or olefinic and contains from about 8 to about 30 carbon atoms. In an embodiment, $R_1$ is ethoxylated. $R_2$, $R_3$ individually hydrogen or a methyl group; $R_4$ and $R_5$ or $R_6$ are individually hydrogen or a hydroxyl group with the provision that at least one of the $R_4$ and $R_5$ or $R_6$ is a hydroxyl groups.

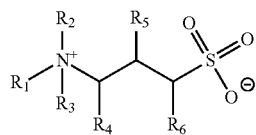

Formula II

In an embodiment, the gelling agent of Formula II is selected from: erucyl amidopropyl hydroxypropyl sulfobetaine:

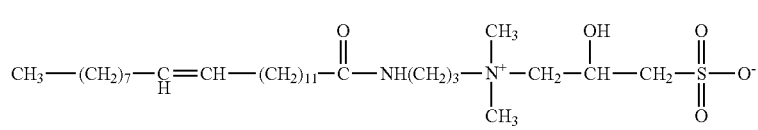

Formula II(a)

and 3-(N-erucamidopropyl-N,N-dimethyl ammonium) propane sulfonate (EDAS):

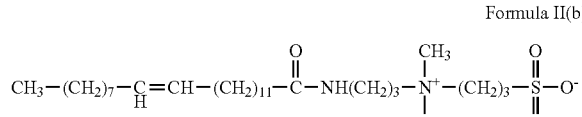

Formula II(b)

In Formula III, $R_1$ is a hydrocarbyl group that may be branched or straight-chain, aromatic, aliphatic or olefinic and contains from about 8 to about 30 carbon atoms. In an embodiment, $R_1$ is ethoxylated. $R_2$, $R_3$ and $R_4$ are the same or different and are alkyl or hydroxyalkyl of from 1 to about 5 carbon atoms, or $R_3$ and $R_4$ or $R_2$ together with the nitrogen atom to which they are bonded form a heterocyclic ring of up to 6 members.

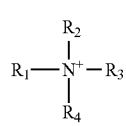

Formula III

In an embodiment, the gelling agent of Formula III is selected from stearyl trimethyl ammonium chloride:

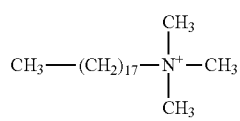

Formula III(a)

and erucyl amidopropyl trimethyl ammonium:

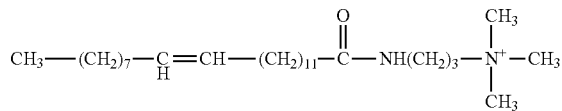

Formula III(b)

In Formula IV, $R_7$ is a saturated or unsaturated, straight or branched chain aliphatic group of from about 7 to about 30 carbon atoms, $R_9$ is a straight or branched chain, saturated or unsaturated divalent alkylene group of from 2 to about 6 carbon atoms, $R_{10}$ and $R_{11}$ are the same or different and are alkyl or hydroxyalkyl of from 1 to about 4 carbon atoms, or $R_{10}$ and $R_{11}$ together with the nitrogen atom to which they are bonded form a heterocyclic ring of up to 6 members, and $R_8$ is hydrogen or a alkyl or hydroxyalkyl group of from 1 to about 4 carbon atoms.

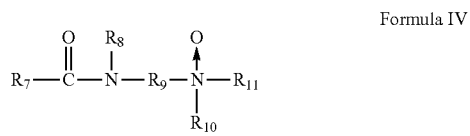

Formula IV

In an embodiment, the gelling agent of Formula IV includes tallow amidopropyl dimethylamine oxide:

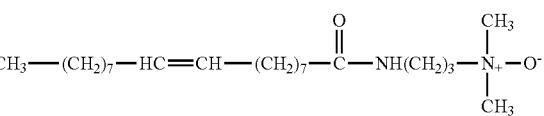

Formula IV(a)

The gelling agent is present in an amount suitable for use in an acidizing process. In an embodiment, the gelling agent is present in an amount from about 0.1 wt % to about 15 wt % by total weight of the fluid. In another embodiment, the gelling agent is present in an amount from about 2.5 wt. % to about 10 wt. % by total weight of the fluid.

In an embodiment, the hydrophobically-modified associative polymer (AP) is water-soluble, but includes one or more water-insoluble short blocks. In an embodiment, the water soluble part is selected from acrylamide, methacrylamide, acrylic acid, methacrylic acid, 2-acrylamidomethylpropanesulfonic acid, N-vinyl pyrrolidone, N-vinyl formamide, and mixtures thereof. In an embodiment, the water insoluble part having hydrophobic properties is selected from straight or branched alkyl or alkylaryl alcohol esters of acrylic or methacrylic acid, straight or branched alkyl or alkylaryl amides of acrylamide or mathacrylamide, styrene, butadiene, 1-vinylnaphthalene and mixtures thereof.

In another embodiment, the hydrophobically-modified associative polymer is a copolymer including monomers selected from anionic monomers, cationic monomers, non-ionic monomers, hydrophobically-modified monomers, and combinations thereof. Non-limiting examples of anionic monomers include acrylic acid and 2-Acrylamido-2-methylpropane sulfonic acid. A non-limiting example of a non-ionic monomer includes acrylamide. A non-limiting example of a cationic monomer includes acryloyloxyethyltrimethylammonium chloride (AETAC). In an embodiment, the hydrophobically-modified monomer is an anionic monomer (e.g. acrylic acid) linked to a hydrophobe via direct carbon-carbon bond, ester bond or amide bond. Non-limiting examples of such hydrophobic monomers include, but not limited to, stearyl acrylate, octadecyl dimethyl allyl ammonium chloride, and n-lauryl-2-methyl-acrylamide.

In an embodiment, the associative hydrophobic monomer of the water-insoluble part possesses a structure selected from formulae (V)-(IX) and combinations thereof.

Formula V wherein $R_1$ is selected from H or $CH_3$ and $R_2$ is selected from
  (i) esters of α,β-ethylenically unsaturated, branched or straight mono- or dicarboxylic acid with $C_2$-$C_{30}$ alkanols (for example n-undecyl (meth)acrylate, ethylhexyl (meth)acrylate);
  (ii) esters of vinyl or allyl alcohol with $C_1$-$C_{30}$ monocarboxylic acids, for example vinyl formate;
  (iii) primary amides of α,β-ethylenically unsaturated mono- and dicarboxylic acids and N-alkyl and N,N-dialkyl derivatives, such as N-propyl(meth)acrylamide;
  (iv) N-vinyllactams and its derivatives, such as N-vinyl-5-ethyl-2-pyrrolidone;
  (v) esters of α,β-ethylenically unsaturated mono- and dicarboxylic acids with aminoalcohols, for example N,N-dimethylaminocyclohexyl(meth)acrylate;
  (vi) amides of α,β-ethylenically unsaturated mono- and dicarboxylic acids with diamines comprising at least one primary or secondary amino group, for example N-[4-(dimethylamino)butyl]acrylamide; and
  (vii) monoolefins ($C_2$-$C_8$) and nonaromatic hydrocarbons comprising at least two conjugated double bonds, for example ethylene, isobutylene and the like.

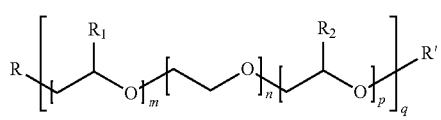

Formula VI where m, n, p and q are integers and m, n, p are less than 150, q is greater than 0, and at least one integer among m, n and p is non-zero, R has a polymerizable vinylic function, $R_1$, and $R_2$ are identical or different, and represent hydrogen atoms or alkyl groups; R' is a hydrophobic group comprising at least 6 and at most 36 carbon atoms, preferentially at least 12 and at most 24 carbon atoms, and very preferentially at least 18 and at most 22 carbon atoms.

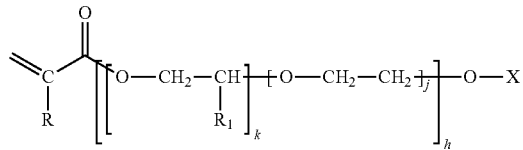

Formula VII where R is H or $CH_3$; wherein $R_1$ is a —$(CH_2)_p$H alkyl chain; wherein p is an integer from 1 to about 4; wherein j is an integer from 1 to about 50; wherein k is an integer from 0 to about 20, wherein h is 1 or 2; and wherein X has the following structure:

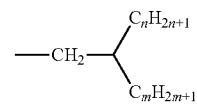

wherein m and n are, independently, positive integers from 1 to 39 and m+n represents an integer from 4 to 40.

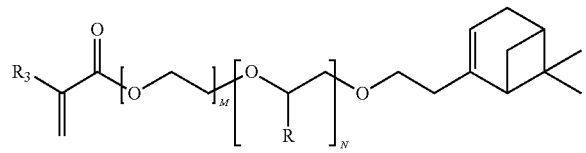

Formula VIII wherein $R_3$ is H or $CH_3$; $R_4$ is an alkyl chain containing 1 to about 4 carbons; M is an integer from 1 to about 50; and N is 0 or an integer of less than or equal to M.

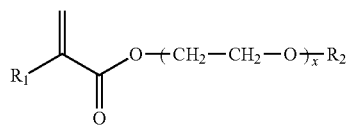

Formula IX wherein $R_1$ is H or $CH_3$; x is an integer from 5 to about 50, $R_2$ is an alkyl chain containing 1 to about 32 carbons or a cycloalkyl ring or a single aromatic 4-6 membered ring.

In an embodiment, the AP is present in an amount sufficient to increase the viscosity of the gelling agent by at least 50% at 100/s, but below its overlap concentration (C*), where C* is 1/intrinsic viscosity. In an embodiment, the AP is present in an amount from about 0.001C* to 0.95C* by total weight of the fluid. Without the AP, the gelling agent by itself does not provide the required viscosity.

In an embodiment, the gelling fluid further includes at least one solvent selected from water, alcohols, and combinations thereof. In an embodiment, the gelling fluid includes an alcohol selected from monohydric alcohols, dihydric alcohols, polyhydric alcohols, and combinations thereof. In another embodiment, the gelling fluid includes an alcohol selected from alkanols, alcohol alkoxylates, and combinations thereof. In another embodiment, the gelling fluid includes an alcohol selected from methanol, ethanol, isopropanol, butanol, propylene glycol, ethylene glycol, polyethylene glycol, and combinations thereof.

Each individual solvent is present in the gelling fluid in an amount suitable for use in an acidizing process. In an embodiment, the amount of each individual solvent in the gelling fluid ranges from 0 wt. % to about 30 wt % by total weight of the fluid, with the total amount of solvent in the formulation ranging from about 10 wt. % to about 70 wt. % by total weight of the fluid.

Optionally, the gelling fluid further includes one or more additives. In an embodiment, the fluid includes one or more additives selected from corrosion inhibitors, iron control agents, clay stabilizers, calcium sulfate inhibitors, mutual solvents, and combinations thereof. In an embodiment, the corrosion inhibitor is selected from alcohols (e.g. acetylenics); cationics (e.g. quaternary ammonium salts, imidazolines, and alkyl pyridines); and nonionics (e.g. alcohol ethoxylates).

In another embodiment, a treatment fluid suitable for use in an acidizing process includes a gelling fluid and an aqueous acid. Suitable aqueous acids include those compatible with gelling agents of Formulas I-IV and the APs for use in an acidizing process. In an embodiment, the aqueous acid is selected from hydrochloric acid, hydrofluoric acid, formic acid, acetic acid, sulfamic acid, and combinations thereof. In an embodiment, the treatment fluid includes acid in an amount up to 30 wt. % by total weight of the fluid.

One embodiment is an oilfield treatment method including the steps of a) providing a fluid containing a surfactant selected from zwitterionic, amphoteric, and cationic surfactants and mixtures of these surfactants, b) adding to the fluid a hydrophobically-modified associative polymer below its C* concentration, wherein in some embodiments the polymer acts as a rheology enhancer and/or internal breaker, and c) injecting the fluid down a well.

In another embodiment, the gelling fluid exhibits the ability to self-break over time without the addition of an internal breaker. In some embodiments, the hydrophobically-modified associative polymer present in the gelling fluid acts as an internal breaker. The function of the internal breaker is to help reduce the viscosity of the gelling fluid over time at reservoir temperature for easy clean up. The polymer acts as a delayed internal breaker, in that, it does not affect the initial properties of the fluid. In another embodiment, the AP contains an ester bond between the polymer backbone and the hydrophobe. The ester bond can hydrolyze over time and act as a breaker for the treatment fluid.

Also provided is a method of acidizing a formation penetrated by a wellbore that includes the steps of injecting into the wellbore at a pressure below formation fracturing pressure a treatment fluid that includes a gelling fluid and an aqueous acid and allowing the treatment fluid to acidize the formation and/or self-divert into the formation. As used herein, the term, "self-divert" refers to a composition that viscosifies as it stimulates the formation and, in so doing, diverts any remaining acid into zones of lower permeability in the formation.

While specific embodiments are discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

The present disclosure will further be described by reference to the following examples. The following examples are merely illustrative and are not intended to be limiting. Unless otherwise indicated, all percentages are by weight of the total composition.

Example 1

Viscosity Enhancement.

To observe the enhancement of the viscosity of the gelling agent by the associative polymer (AP), a gelling fluid was prepared and analyzed as follows. Amounts of gelling agent of Formula I (1.5% active) and AP of the type acrylic acid (AA)-2-acrylamidomethylpropanesulfonic acid (AMPS)-ethylhexyl acrylate (EHA) (0.15 wt. % total polymer, C*=1.37 wt. %) were blended first in water and $CaCl_2$ (30 wt. % of $CaCl_2$ based on total weight of the composition). Once all the components were added, blending at 7000 rpm was continued for another 4 minutes. The blended gelling fluid was centrifuged until bubbles were no longer observed. Then, the fluid was tested on a high pressure high temperature rheometer. In one embodiment, a Brookfield rheometer was used for testing where the gelling fluid was sheared at a constant shear rate of 100/s while performing a temperature ramp at 2.5° F./min. FIG. 1 shows the viscosity enhancement of the surfactant upon addition of the AP.

Example 2

Viscoelasticity.

The addition of AP to the surfactant also imparts viscoelasticity to the fluid. A fluid is considered to be viscoelastic if at least one of the following tests is satisfied.

Figure 2:
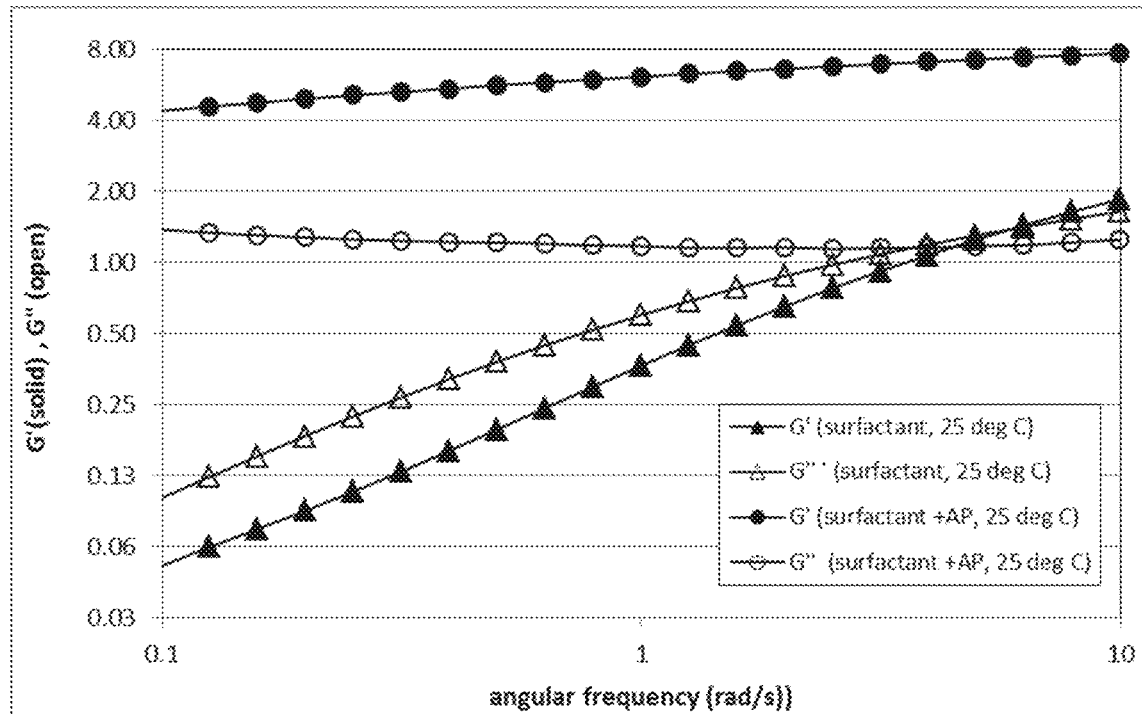
FIG. 2 is a plot showing storage and loss moduli of gelling agent surfactant and gelling agent surfactant+AP in 22.8 wt. % $CaCl_2$.

Viscoelasticity can be measured by swirling a fluid to create bubbles in the fluid and then visually observing whether the bubbles recoil after the swirling is stopped. If an air bubble suspended in the fluid recoils and comes back to its original position without moving to the air/fluid interface, then the fluid is considered to be viscoelastic. Otherwise, the fluid does not possess viscoelastic properties. Another method of determining viscoelasticity of a fluid is by measuring its elastic (or storage) and viscous (loss) moduli. As defined in U.S. Publication No. 2011/0105369: "elastic modulus (G') is a measure of the tendency of a substance to be deformed elastically (i.e., non-permanently) when a force is applied to it and returned to its normal shape." Whereas the loss modulus (G") is a measure of the energy lost when a substance is deformed. Both are expressed in units of pressure, for example, Pa (Pascals) or dynes/$cm^2$. If G'>G" over a frequency range of 0.1-10 rad/s at a given temperature, then the fluid is considered to be viscoelastic at that temperature. Based on the bubble recoil test and results shown in FIG. 2, it is clear that the addition of AP to the surfactant imparts viscoelasticity to the surfactant.

Example 3

Internal Breaker.

Figure 3:
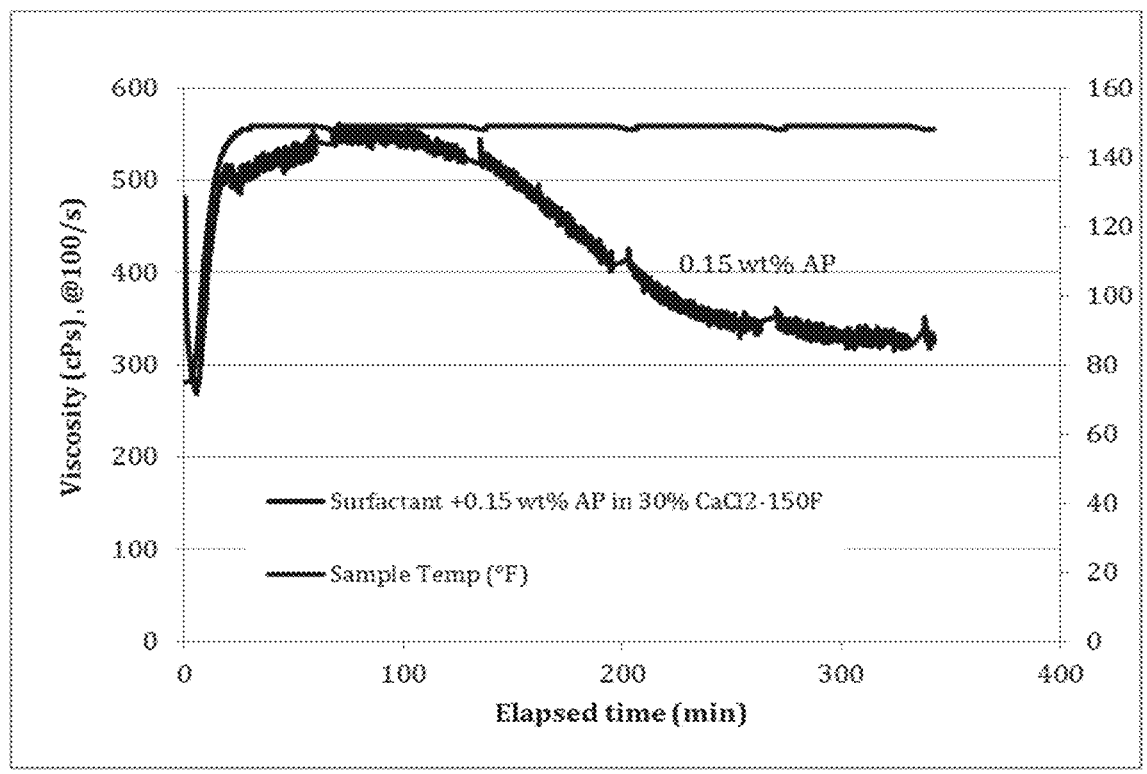
FIG. 3 is plot showing a slow decrease in viscosity over time, indicating that the AP acts as a delayed internal breaker.

The hydrophobically-modified associative polymer present in the gelling fluid can act as an internal breaker. The function of the internal breaker is to help reduce the viscosity of the gelling fluid over time at reservoir temperature for easy clean up. As seen in FIG. 3, there is a gradual decrease of the viscosity over time at the specified temperature of 150° F. The polymer acts as a delayed internal breaker, in that, it does not affect the initial properties of the fluid for the first 100 minutes.

Example 4

Acid Compatibility.

In another embodiment, the compatibility of the gelling fluid of Example 1 in spent acid with acid additives was investigated in order to ensure that the presence of commonly used acid additives does not affect performance. Such additives include corrosion inhibitors, emulsifiers, chelating agents, iron control agents (chelating or reducers).

Figure 4:
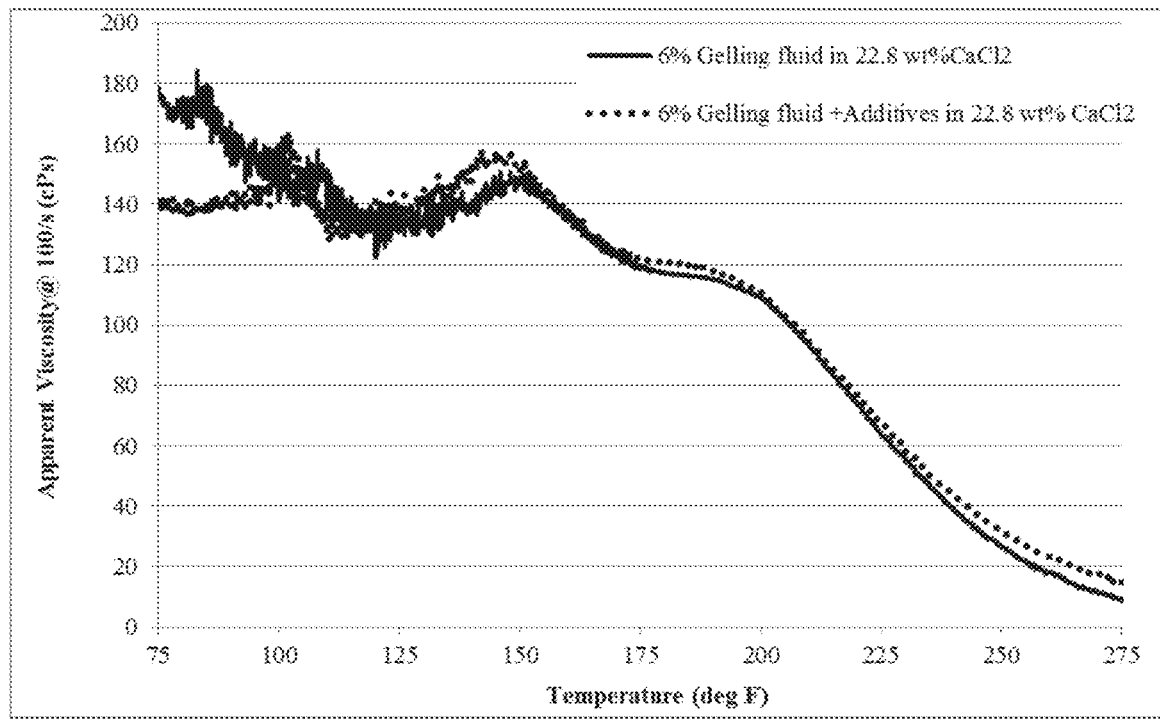
FIG. 4 is a plot of apparent viscosity as a function of temperature for a 6% gelling fluid from Example 1 with and without acid additives.

The gelling fluid of Example 1 was blended with acid additives in $CaCl_2$ solution at high shear rate (7000-10000 rpm) and the resulting blend was centrifuged to remove any bubbles. The obtained gel was tested under pressure at a constant shear rate of 100/s using a high pressure high temperature rheometer from room temperature to the desired temperature. FIG. 4 shows the compatibility of 6% of the gelling agent of Formula I in 22.8 wt. % $CaCl_2$, which corresponds to 15% HCl being totally spent. The solid line corresponds to the gelling fluid formulation without additives; the dotted lines correspond to the formulation with a corrosion inhibitor, a non-emulsifier and chelating agent.

Example 5

Corrosion Studies.

In acidizing with strong acids, such as hydrochloric acid, corrosion is a major challenge to control especially at elevated temperatures. The corrosion rate of 15% HCl and 20% HCl containing a 6 vol % of the gelling agent from Example 1 was determined in the presence of corrosion inhibitor, nonemulsifier and iron control agents. The corrosion rate was determined by the weight method using N-80 coupons at 200° F. after 6 hours. Table 1 shows a very acceptable level of protection against acid corrosion (≤0.05 $lb_m/ft^2$).

TABLE 1

Corrosion data for 15 wt. % and 20 wt. % HCl containing a 6 vol. % of the gelling fluid from Example 1 at 200° F. after 6 hours.

|  | Accepted corrosion limit | 15% HCl | 20% HCl |
|---|---|---|---|
| Corrosion rate $lb_m/ft^2$ | 0.05 | 0.027 | 0.039 |

Example 6

Dual Corefloods.

The ultimate goal of the gelling fluid acid system is to divert acid flow from high permeability zones to lower permeability zones to increase the effectiveness of the stimulation treatment. Two dual (parallel) core flood experiments were conducted at 200° F. to evaluate the ability of a gelling fluid of the present disclosure to divert the acidizing fluid effectively. A dual core flood experiment imitates the injection of the treatment (e.g. stimulation) fluid into a formation with a contrast in permeability of its producing zones. In this case, acid diversion is required to ensure that the acid is flowing through, and hence, stimulating all zones.

Two Indiana limestone cores (1.5" diameter×6" length) representing high- and low-permeability layers were used. The properties of each core are listed in Table 2 and Table 3 for 15 and 20 wt. % HCl, respectively. The compositions of the stimulation fluids are shown in Table 4.

TABLE 2

Initial properties of the two cores used in the coreflood for 15% HCl at 200° F.

| Core | Porosity, % | Initial Permeability, md | K-Ratio |
|---|---|---|---|
| HP | 14.8 | 34.45 | 2.67 |
| LP | 14.2 | 12.47 | |

TABLE 3

Initial properties of the two cores used in the coreflood for 20% HCl at 200° F.

| Core | Porosity, % | Initial Permeability, md | K-Ratio |
|---|---|---|---|
| HP | 16.13 | 40.42 | 2.16 |
| LP | 15.05 | 18.7 | |

TABLE 4

Acid composition used for the dual corefloods at 200° F.

| HCl | 15 wt % | 20 wt % |
|---|---|---|
| Gelling agent (Example 1) | 6 vol % | 6 vol % |
| Corrosion Inhibitor | 10 gpt | 10 gpt |
| Non-emulsifier | 1 gpt | 1 gpt |
| Corrosion intensifier (solid) | 50 pptg | 50 pptg |
| Iron chelating agent | 1 gpt | 1 gpt |

During the experiment, the pressure drop across both cores was recorded as a function of the injected pore volume. Samples of the flow at the effluent of each core were collected periodically as a function of time. The collected volumes were used to determine the percentage of flow through each core during the course of the experiment. Post treatment, both cores were imaged using a CT-scan technique to visualize the extent and the structure of the created voids (e.g. wormholes) in each core.

Figure 5:
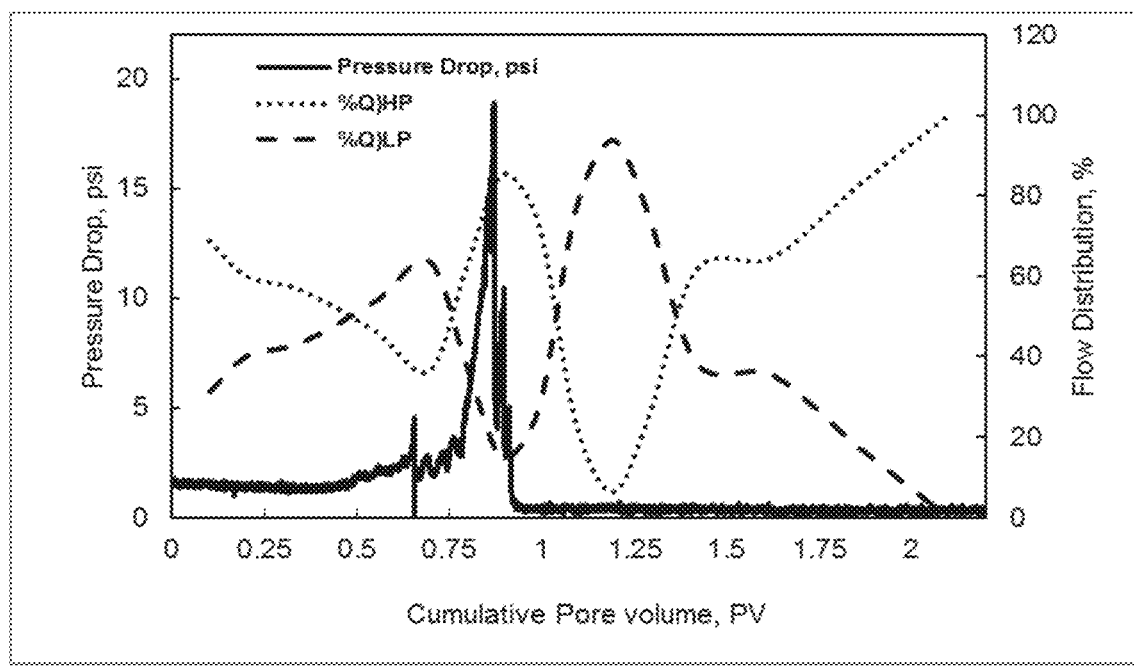
FIG. 5 is a plot depicting the pressure drop profile for 15% HCl.
Figure 6:
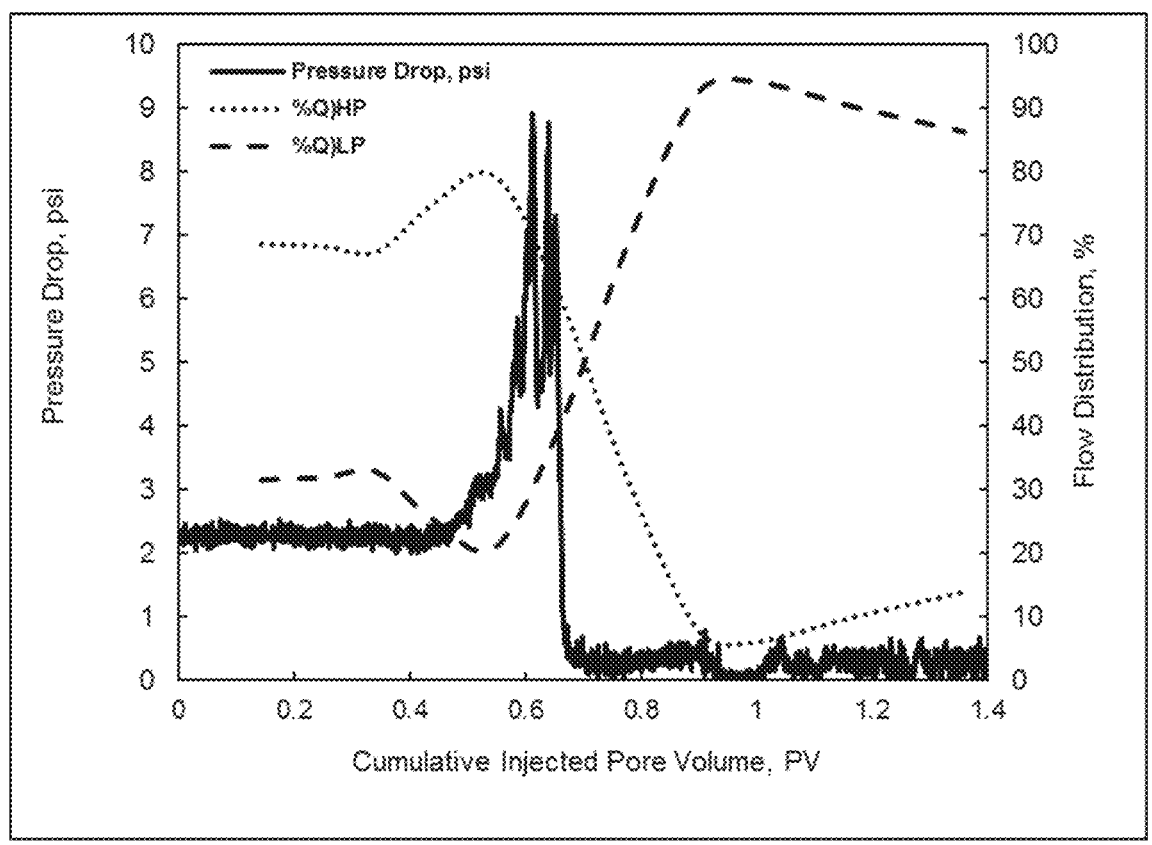
FIG. 6 is a plot depicting the pressure drop profile for 20% HCl.

The pressure drop profiles for the 15 and 20 wt. % HCl coreflood studies are depicted in FIG. 5 and FIG. 6, respectively, along with the flow distribution curves. The terms Q, HP and LP stands for flow rate, high permeability and low permeability, respectively.

The data shows a proper degree of diversion supported by the increase in the magnitude of the pressure drop. A maximum increase in pressure drop from the baseline indicates a viscosity build up and gel formation for both cases. Additional evidence of diversion is the distribution of the flow between the two cores, representing the two high- and low-permeability layers in the formation. The flow through the high-permeability cores declines, while the flow in the low-permeability core increase and as a result, one or more crossing points were observed. These cross points indicate that the low-permeability core is accepting more flow due to the increase in the pressure drop in the high-permeability core as a result of the viscosity build up and gel formation.

Figure 7:
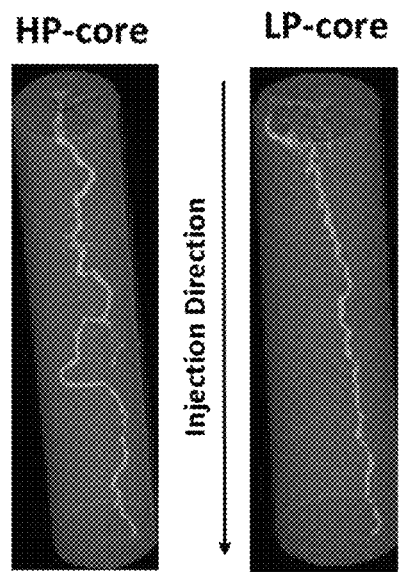
FIG. 7 provides post-treatment CT-scan images for 15% HCl coreflood at 200° F.
Figure 8:
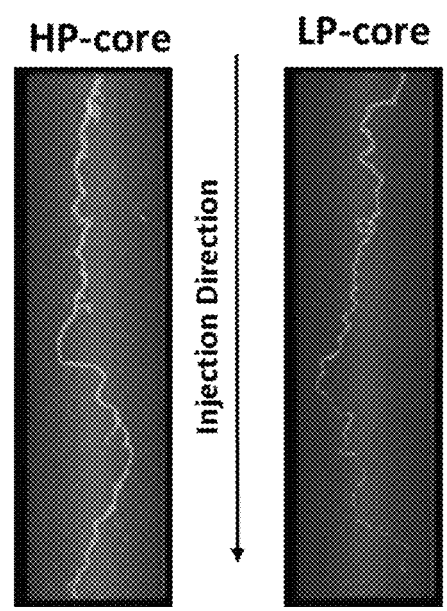
FIG. 8 provides post-treatment CT-scan images for 20% HCl coreflood at 200° F.

The post-treatment CT-scans provide additional evidence of a successful diversion of 15 and 20 wt. % HCl as shown in FIG. 7 and FIG. 8, respectively. The images demonstrate that the acid injection resulted in a complete stimulation (breakthrough) in the low- and high-permeability cores. The majority of the initial stage of acid injection, which was flowing into the high-permeability core, was successful in diverting the acid into the low-permeability core and due to the definite length of each core (6 inch), a breakthrough occurred in both cores. FIGS. 7 and 8 also show a significant degree of tortuosity in the high-permeability core indicating a successful gel formation that forced the acid to change the reaction path and flow in higher proportion into the low-permeability core. These results show the applicability of the new gelling fluid as an effective diverting agent for acid treatments at moderate and elevated temperatures.

The disclosed subject matter has been described with reference to specific details of particular embodiments thereof. It is not intended that such details be regarded as limitations upon the scope of the disclosed subject matter except insofar as and to the extent that they are included in the accompanying claims.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components, substances and steps. As used herein the term "consisting essentially of" shall be construed to mean including the listed components, substances or steps and such additional components, substances or steps which do not materially affect the basic and novel properties of the composition or method. In some embodiments, a composition in accordance with embodiments of the present disclosure that "consists essentially of" the recited components or substances does not include any additional components or substances that alter the basic and novel properties of the composition. If there is any conflict in the usages of a word or term in this specification and one or more patent or other documents that may be incorporated herein by reference, the definitions that are consistent with this specification should be adopted.

We claim:

1. A method of acidizing a formation penetrated by a wellbore comprising the steps of:
   a. injecting into the wellbore at a pressure below formation fracturing pressure a treatment fluid comprising a gelling fluid comprising a gelling agent and a hydrophobically-modified associative polymer, and an aqueous acid, wherein the hydrophobically-modified associative polymer comprises a polymer backbone, at least one water-soluble part, at least one water-insoluble part comprising ethylhexyl acrylate, and an ester bond between the polymer backbone and the water-insoluble part;
   b. allowing the treatment fluid to acidize the formation; and
   c. allowing the ester bond to hydrolyze over time and act as a breaker for the treatment fluid.

2. The method of claim 1 further comprising the step of allowing the treatment fluid to self-divert into the formation.

3. The method of claim 1, wherein the gelling agent comprises a surfactant according to Formula I:

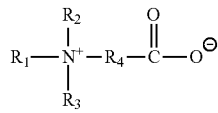

Formula I wherein $R_1$ is selected from the group consisting of alkyl, alkenyl, alkylarylalkylene, alkenylarylalkylene, alkylaminoalkylene, alkenylamino-alkylene, alkylamidoalkylene, and alkenylamidoalkylene, wherein each of said alkyl groups contain from about 14 to about 24 carbon atoms and wherein said alkylene groups contain from about 1 to about 6 carbon atoms; and $R_2$, $R_3$ and $R_4$ are the same or different and are alkyl or hydroxyalkyl of from 1 to about 5 carbon atoms, or $R_3$ and $R_4$ or $R_2$ together with the nitrogen atom to which they are bonded form a heterocyclic ring of up to 6 members.

4. The method of claim 1, wherein the gelling agent comprises a surfactant according to Formula II:

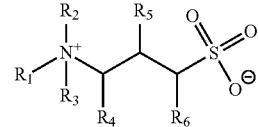

Formula II wherein $R_1$ is a hydrocarbyl group and contains from about 8 to about 30 carbon atoms; $R_2$ and $R_3$ are individually hydrogen or a methyl group; $R_4$ and $R_5$ or $R_6$ are individually hydrogen or a hydroxyl group with the provision that at least one of the $R_4$ and $R_5$ or $R_6$ is a hydroxyl groups.

5. The method of claim 1, wherein the gelling agent comprises a surfactant according to Formula III:

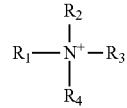

Formula III wherein $R_1$ is a hydrocarbyl group and contains from about 8 to about 30 carbon atoms; and $R_2$, $R_3$ and $R_4$ are the same or different and are alkyl or hydroxyalkyl of from 1 to about 5 carbon atoms, or $R_3$ and $R_4$ or $R_2$ together with the nitrogen atom to which they are bonded form a heterocyclic ring of up to 6 members.

6. The method of claim 1, wherein the gelling agent comprises a surfactant according to Formula IV:

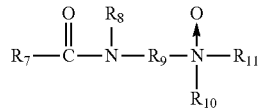

Formula IV wherein $R_7$ is an aliphatic group of from about 7 to about 30 carbon atoms; $R_9$ is a divalent alkylene group of from 2 to about 6 carbon atoms; $R_{10}$ and $R_{11}$ are the same or different and are alkyl or hydroxyalkyl of from 1 to about 4 carbon atoms, or $R_{10}$ and $R_{11}$ together with the nitrogen atom to which they are bonded form a heterocyclic ring of up to 6 members; and $R_8$ is hydrogen or a alkyl or hydroxyalkyl group of from 1 to about 4 carbon atoms.

7. The method of claim 1, wherein the at least one water-soluble part selected from the group consisting of acrylamide, methacrylamide, acrylic acid, methacrylic acid, 2-acrylamidomethylpropanesulfonic acid, N-vinyl pyrrolidone, N-vinyl formamide, and mixtures thereof.

8. The method of claim 1, wherein the hydrophobically-modified associative polymer is present in an amount from about 0.001C* to 0.95C* by total weight of the gelling fluid.

9. The method of claim 1, wherein the gelling fluid further comprises at least one solvent selected from the group consisting of water, alcohols, and combinations thereof.

10. A method of treating an oilfield well comprising the steps of injecting into the well a fluid comprising: (i) a gelling agent and (ii) a hydrophobically-modified associative polymer in an amount below its C* concentration, wherein the hydrophobically-modified associative polymer comprises a polymer backbone, at least one water-soluble part, at least one water-insoluble part comprising ethylhexyl acrylate, and an ester bond between the polymer backbone and the water-insoluble part; and allowing the ester bond to hydrolyze over time and act as a breaker for the treatment fluid.

11. The method of claim 10, wherein the gelling agent comprises a surfactant according to Formula I:

Formula I

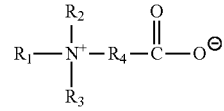

wherein $R_1$ is selected from the group consisting of alkyl, alkenyl, alkylarylalkylene, alkenylarylalkylene, alkylaminoalkylene, alkenylamino-alkylene, alkylamidoalkylene, and alkenylamidoalkylene, wherein each of said alkyl groups contain from about 14 to about 24 carbon atoms and wherein said alkylene groups contain from about 1 to about 6 carbon atoms; and $R_2$, $R_3$ and $R_4$ are the same or different and are alkyl or hydroxyalkyl of from 1 to about 5 carbon atoms, or $R_3$ and $R_4$ or $R_2$ together with the nitrogen atom to which they are bonded form a heterocyclic ring of up to 6 members.

* * * * *